United States Patent
Bryans et al.

(10) Patent No.: US 6,465,689 B1
(45) Date of Patent: Oct. 15, 2002

(54) STEREOSELECTIVE PROCESSES FOR THE PREPARATION OF GABAPENTIN ANALOGUES

(75) Inventors: Justin Stephen Bryans, Balsham; Andrew Ian Morrell, Kent, both of (GB)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 09/445,633

(22) PCT Filed: Aug. 11, 1998

(86) PCT No.: PCT/US98/16652

§ 371 (c)(1),
(2), (4) Date: Dec. 8, 1999

(87) PCT Pub. No.: WO99/14184

PCT Pub. Date: Mar. 25, 1999

Related U.S. Application Data
(60) Provisional application No. 60/059,204, filed on Sep. 18, 1997.

(51) Int. Cl.$^7$ ................................................ C07C 61/08
(52) U.S. Cl. ...................... 562/507; 560/125; 560/128; 518/543
(58) Field of Search ................................ 560/125, 128; 562/507; 548/543

(56) References Cited

U.S. PATENT DOCUMENTS
5,091,567 A   2/1992   Geibel et al. ................ 562/507

FOREIGN PATENT DOCUMENTS
| | | |
|---|---|---|
| EP | 0414274 | 2/1991 |
| WO | 9729101 | 8/1997 |
| WO | 9733859 | 9/1997 |

*Primary Examiner*—Paul J. Killos
(74) *Attorney, Agent, or Firm*—Charles W. Ashbrook

(57) ABSTRACT

This invention is novel processes for the stereoselective preparation of gabapentin analogues.

5 Claims, No Drawings

STEREOSELECTIVE PROCESSES FOR THE PREPARATION OF GABAPENTIN ANALOGUES

This application claims the benefit of Provisional application Ser. No. 60/059,204, filed Sep. 18, 1997.

BACKGROUND OF THE INVENTION

U.S. Pat. No. 5,091,567, hereby incorporated by reference, covers a process for the preparation of gabapentin (1-aminomethyl-1-cyclohexane-acetic acid)

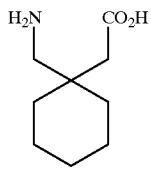

which medicament is useful, for example, in the treatment of epilepsy. The process is illustrated by the scheme:

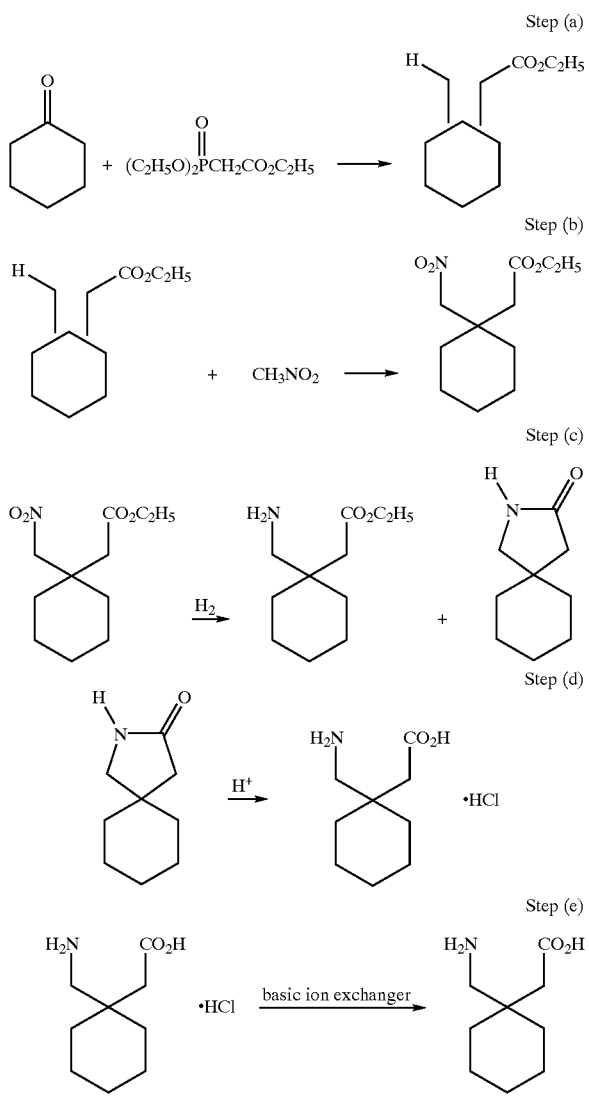

The instant invention provides a stereoselective synthesis for the ring-substituted analogs of gabapentin and to gabapentin itself. The advantages of the instant syntheses are: control of stereochemistry and no resolution is required at the end of the synthesis.

SUMMARY OF THE INVENTION

The invention encompasses a novel synthetic route for the preparation of substituted gabapentin analogues. The route enables the synthesis of certain single stereoisomers of individual alkylated gabapentin derivatives with a high degree of stereochemical purity.

The invention is outlined in the general route shown below. The first step involves conversion of a substituted cyclohexanone to an (α,β-unsaturated ester via use of a trialkylphosphonoacetate or an (alkoxycarbonylmethyl) triphenyl-phosphonium halide and a base, such as sodium hydride, potassium hydride, lithium- or sodium- or potassium-hexamethyldisilazide, butyllithium or potassium t-butoxide in a solvent such as tetrahydrofuran, dimethylformamide, diethylether, or dimethylsulfoxide at a suitable temperature in the range from −78° C. to 100° C.

The second step involves reaction of the α,β-unsaturated ester with nitromethane and a suitable base such as tetrabutylammonium fluoride, tetra-methylguanidine, 1,5-diazabicyclo[4,3,0]non-5-ene, 1,8-diazabicyclo[5,4,0]undec-7-ene, a sodium or potassium alkoxide, sodium hydride or potassium fluoride in a solvent such as tetrahydrofuran, diethylether, dimethylformamide, dimethylsulphoxide, benzene, toluene, dichloromethane, chloroform, or tetrachloromethane at a suitable temperature in the range from −20° C. to 100° C.

The third step involves catalytic hydrogenation of the nitro moiety using a catalyst such as Raney nickel, palladium on charcoal or rhodium catalyst or other nickel or palladium containing catalyst in a solvent such as methanol, ethanol, isopropanol, ethyl acetate, acetic acid, 1,4-dioxane, chloroform or diethyl ether at a suitable temperature in the range from 20° C. to 80° C.

The final step involves a hydrolysis using hydrochloric acid and may also utilize a cosolvent such tetrahydrofuran or 1,4-dioxane or other such inert water miscible solvent at a suitable temperature in the range from 20° C. to reflux.

General scheme:

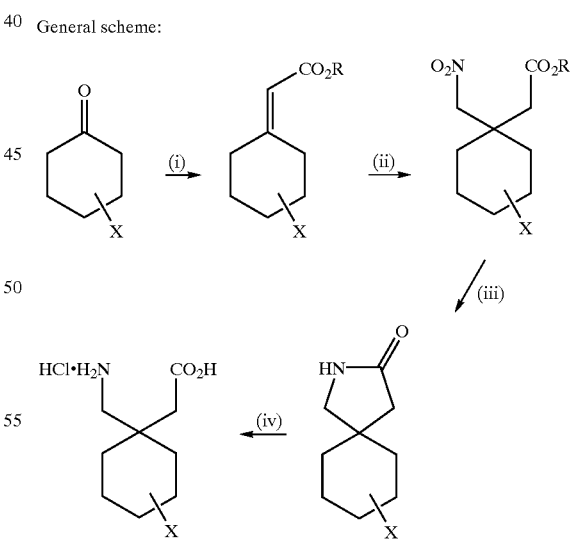

DETAILED DESCRIPTION OF THE INVENTION

The following experimental procedures provide a novel route to be used to stereoselectively synthesize gabapentin and analogues thereof. This route provides access to pure stereoisomers.

Example 1 below shows the route used to synthesize gabapentin itself. This route is also useful in the synthesis of compounds of formula

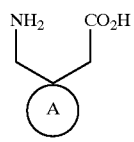

(I)

a pharmaceutically acceptable salt thereof or a prodrug thereof wherein A is a bridged ring selected from

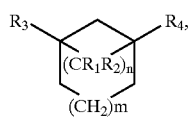

(1)

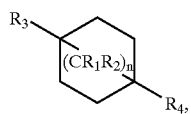

(2)

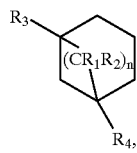

(3)

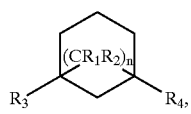

(4)

and

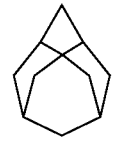

(5)

wherein
  $R_1$ and $R_2$ are each independently selected from hydrogen and methyl;
  $R_3$ and $R_4$ are each independently selected from hydrogen or methyl;
  n is an integer of from 1 to 4; and
  m is an integer of from 0 to 2.

The route is further useful in the synthesis of compounds of formula

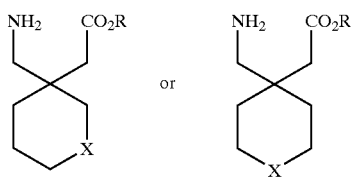

(II)

or a pharmaceutically acceptable salt thereof wherein:
  X is O, S, S(O), S(O)$_2$, or NR$_1$ wherein R$_1$ is hydrogen, straight or branched alkyl of from 1 to 6 carbon atoms, benzyl, —C(O)R$_2$ wherein R$_2$ is straight or branched alkyl of from 1 to 6 carbon atoms, benzyl, or phenyl, or —CO$_2$R$_3$ wherein R$_3$ is straight or branched alkyl of from 1 to 6 carbon atoms, or benzyl wherein the benzyl and the phenyl groups can be unsubstituted or substituted by from 1 to 3 substituents each independently selected from halogen, CF$_3$, and nitro; and
  R is hydrogen or lower alkyl.

Example 2 below shows the use of a 4-substituted cyclohexanone to provide a pure trans gabapentin analog.

Example 3 below shows the use of a disubstituted cyclohexanone.

Example 4 below shows the use of a 3-substituted gabapentin analog to provide a pure cis product which is a mixture of enantiomers. The use of an enantiomerically pure 3-substituted cyclohexanone provides a pure product.

General Route

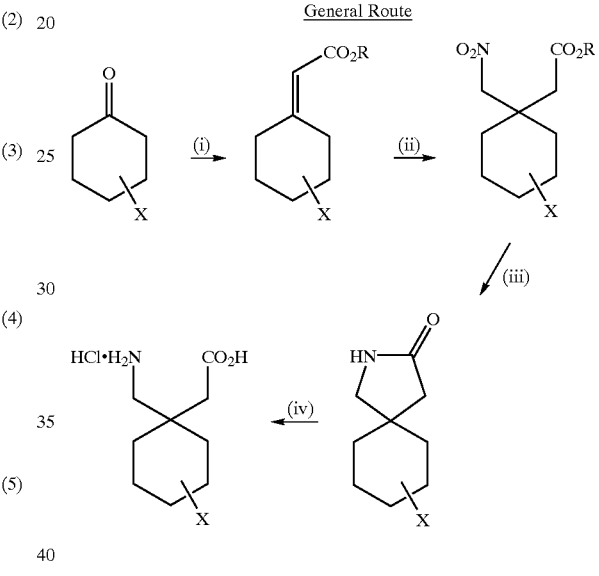

Reagents and Conditions (i) (R$^1$O)$_2$P(O)CH$_2$CO$_2$R, base (e.g., NaH, LiN(SiMe$_3$)$_2$, K,H BuLi)

(ii) MeNO$_2$, base (e.g., Bu$_4$N$^+$F, tetramethylguanidine, KF)

(iii) Catalytic hydrogenation using, for example, Raney nickel or Palladium on charcoal)

(iv) Hydrolysis using HCl

EXAMPLE 1

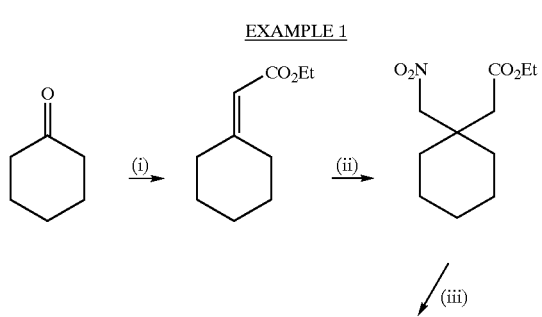

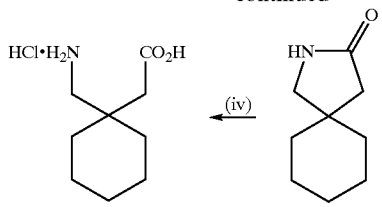

(i) (EtO)$_2$P(O)CH$_2$CO$_2$Et, NaH, THF
(ii) MeNO$_2$, Bu$_4$N$^+$F$^-$, THF, 70° C.
(iii) Raney Ni, H$_2$, MeOH
(iv) HCl/H$_2$O α,β-unsaturated Ester Sodium hydride (60% dispersion in oil, 1.16 g, 28.99 mmol) was suspended in dry tetrahydrofuran (40 mL) and cooled to 0° C. Triethyl phosphonoacetate (6.35 mL, 31.89 mmol) was added. Once the effervescence had subsided the mixture was stirred at 0° C. for 15 minutes. Cyclohexanone (3 mL, 28.99 mmol) was then added and the mixture allowed to warm to room temperature. After 1 hour the mixture was partitioned between 2N HCl (50 mL) and diethyl ether (100 mL). The ether layer was collected, washed with brine. dried (MgSO$_4$), and the solvent removed in vacuo to give a clear oil which was purified by flash chromatography (silica, ethyl acetate:heptane 1:9) to yield 3.8 g (78%) of a colorless oil which was used without further purification.

Nitro Ester

The α,β-unsaturated ester (1.605 g, 9.55 mmol) was dissolved in tetrahydrofuran (30 mL) with nitromethane (1.03 mL, 19.1 mmol) and tetrabutylammonium fluoride (1.0 M in THF, 14 mL, 14.0 mmol) and the resulting mixture heated to 70° C. After 18 hours the mixture was diluted with ethyl acetate (60 mL) and washed with 2N HCl (40 mL) followed by brine (40 mL). The organic phase was separated, dried (MgSO$_4$), and the solvent removed in vacuo. The residue was purified by flash chromatography (silica, ethyl acetate:heptane, 1:9) to give 996 mg (46%) as a colorless oil.

$^1$H NMR 400 MHz (CDCl$_3$) δ1.27 (3H, t, J=6 Hz), 1.38–1.62 (10H, m), 2.54 (2H, s), 4.15 (2H, q, J=6 Hz), 4.70 (2H, s).

MS (ES$^+$) m/e: 230 ([MH]$^+$; 78%), 170 (100%)

IR thin film v (cm$^{-1}$): 1031, 1180, 1377, 1548, 1732, 2935.

C$_{11}$H$_{19}$NO$_4$ calculated: C, 57.63%; H, 8.35%; N, 6.11%
Found: C, 57.88%; H, 8.61%; N, 6.01%

Lactam

The nitro ester (935 mg, 4.08 mmol) was dissolved in methanol (40 mL) and shaken over Raney nickel (catalytic) under an atmosphere of hydrogen gas (40 psi) at 35° C. After 18 hours the catalyst was removed by filtration through celite. The methanol was removed in vacuo to give 622 mg (100%) of an oil which crystallized on standing.

$^1$H NMR 400 MHz (CDCl$_3$) δ: 1.38–1.61 (10H, m), 2.18 (2H, s), 3.14 (2H, s), 5.61 (1H, brs).

MS (ES$^+$) m/e: 154 ([MH]$^+$; 100%)

IR thin film v (cm$^{-1}$): 1252, 1451, 1695, 2925.

C$_9$H$_{15}$NO calculated: C, 70.55%; H, 9.87%; N, 9.14%
Found: C, 70.46%; H, 9.72%; N, 8.97%

Amino Acid Hydrochloride

The lactam (608 mg, 4.0 mmol) was heated to reflux in a mixture of 6N HCl (15 mL) and 1,4-dioxan (5 mL). After 4 hours the solvent was removed in vacuo and the solid residue recrystallized from a methanol/ethyl acetate/heptane mixture to give 682 mg (71%) of a white solid.

$^1$H NMR 400 MHz (d-6 DMSO) δ: 1.12–1.51 (10H, m), 2.41 (2H, s), 2.91 (2H, s), 8.06 (3H, br s), 12.36 (1H, br s).

MS (APCI) m/e: 172 ([MH−HCl]$^+$; 100%)

C$_9$H$_{18}$NO$_2$Cl calculated: C, 52.05%; H, 8.74%; N, 6.74%; Cl, 17.07%
Found: C, 51.97%; H, 8.77%; N, 6.63%; Cl, 16.94%

EXAMPLE 2

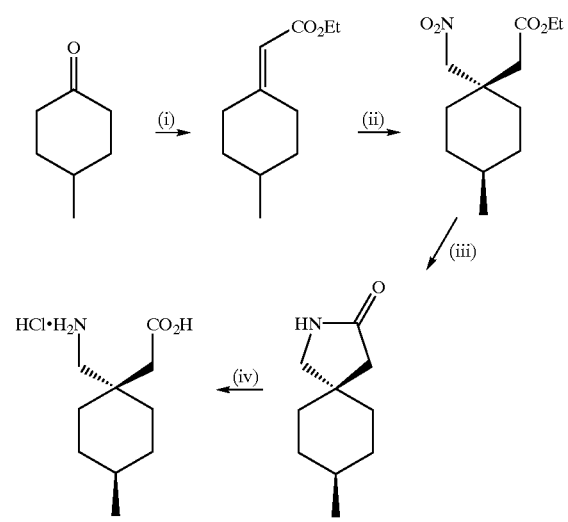

(i) (EtO)$_2$ P(O)CH$_2$CO$_2$Et, NaH, THF
(ii) MeNO$_2$, Bu$_4$N$^+$F$^-$, THF, 70° C.
(iii) Raney Ni, H$_2$, MeOH
(iv) HCl/H$_2$O α,β-unsaturated Ester Sodium hydride (60% dispersion in oil, 0.98 g, 24.45 mmol) was suspended in dry tetrahydrofuran (50 mL) and cooled to 0° C. Triethyl phosphonoacetate (5.12 mL, 25.67 mmol) was added. Once the effervescence had subsided the mixture was stirred at 0° C. for 15 minutes. 4-Methyl cyclohexanone (3 mL, 24.45 mmol) was then added and the mixture allowed to warm to room temperature. After 1.5 hours the solvent was decanted from the thick oil which had formed and the oil washed with diethyl ether (3×50 mL). The decanted solvent and the ether washings were combined and washed with 2N HCl (50 mL) followed by brine (50 mL), dried (MgSO$_4$), and the solvent removed in vacuo to give a clear oil which was used without purification.

Trans-Nitro Ester

The α,β-unsaturated ester (2.94 g, 16.15 mmol) was dissolved in tetrahydrofuran (20 mL) with nitromethane (1.75 mL, 32.3 mmol) and tetrabutylammonium fluoride (1.0 M in THF, 24 mL, 24.0 mmol) and the resulting mixture heated to 70° C. After 18 hours the mixture was diluted with ethyl acetate (60 mL) and washed with 2N HCl (40 mL) followed by brine (40 mL). The organic phase was separated, dried (MgSO$_4$), and the solvent removed in vacuo. The residue was purified by flash chromatography (silica, ethyl acetate:heptane, 1:9) to give 2.74 g (70%) as a colorless oil.

$^1$H NMR 400 MHz (CDCl$_3$) δ: 0.93 (3H, d, J=6 Hz), 1.08–1.23 (8H, m), 1.58 (2H, m), 1.73 (2H, m), 2.59 (2H, s), 4.15 (2H, q, J=6 Hz), 4.60 (2H, s).

MS (APCI) m/e: 244 ([MH]$^+$; 8%), 198 (100%), 183 (68%), 168 (66%)

IR thin film v (cm$^{-1}$): 1029, 1179, 1195, 1377, 1457, 1549, 1732, 2929.

C$_{12}$H$_{21}$NO$_4$ calculated: C, 59.24%; H, 8.70%; N, 5.76%
Found: C, 59.00%; H, 8.73%; N, 5.70%

Lactam

The nitro ester (2.70 g, 4.08 mmol) was dissolved in methanol (60 mL) and shaken over Raney nickel (catalytic) under an atmosphere of hydrogen gas (40 psi) at 35° C. After 18 hours the catalyst was removed by filtration through celite. The methanol was removed in vacuo and the residue purified by flash chromatography (silica, ethyl acetate/heptane 1:1) to give 721 mg (39%) of a white solid.

$^1$H NMR 400 MHz (CDCl$_3$) δ: 0.91 (3H, d, J=6 Hz), 0.94–1.12 (2H, m), 1.25–1.43 (3H, m), 1.60 (2H, m), 1.71 (2H, br d, J=16 Hz), 2.21 (2H, s), 3.10 (2H, s), 5.64 (1H, br s).

MS (APCI) m/e: 168 ([MH]$^+$; 100%)

IR thin film v (cm$^{-1}$): 1254, 1305, 1446, 1494, 1668, 1693, 2910, 3219.

C$_{10}$H$_{17}$NO calculated: C, 71.18%; H, 10.25%; N, 8.37%
Found: C, 71.76%; H, 10.33%; N, 8.10%

Amino Acid Hydrochloride

The lactam (715 mg, 4.0 mmol) was heated to reflux in a mixture of 6N HCl (15 mL) and 1,4-dioxan (5 mL). After 4 hours the solvent was removed in vacuo and the solid residue recrystallized from a methanol/ethyl acetate/heptane mixture to give 664 mg (70%) of a white solid.

$^1$H NMR 400 MHz (d-6 DMSO) δ: 0.88 (3H, d, J=6 Hz), 1.10 (2H, m), 1.22 (3I–1, m), 1.22 (3H, m), 1.51 (2H, m), 2.43 (2H, s), 2.85 (2H, s), 7.92 (3H, br s), 12.39 (1H, br s).

MS (APCI) m/e: 186 ([MH–HCl]$^+$; 100%)

C$_{10}$H$_{20}$NO$_2$Cl calculated: C, 54.17%; H, 9.09%; N, 6.32%; Cl, 15.99%
Found: C, 54.33%; H, 9.38%; N, 6.32%; Cl, 15.78%

EXAMPLE 3

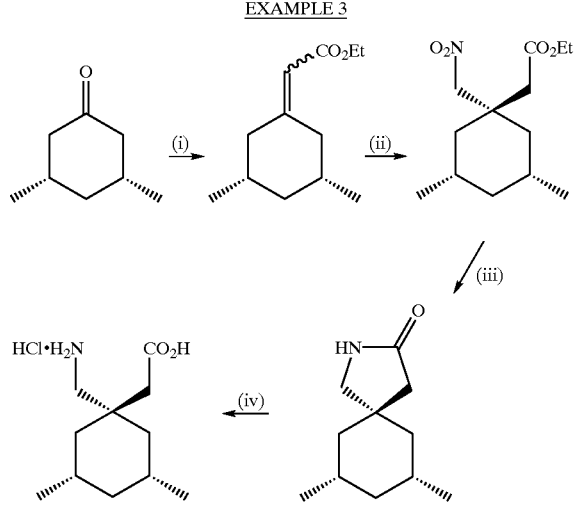

(i) (EtO)$_2$ P(O)CH$_2$CO$_2$Et, NaH, THF
(ii) MeNO$_2$, Bu$_4$N$^+$F, THF, 70° C.
(iii) Raney Ni, H$_2$, MeOH
(iv) HCl/H$_2$O α,β-unsaturated Ester Sodium hydride (60% dispersion in oil, 1.029 g, 25.7 mmol) was suspended in dry tetrahydrofuran (50 ml,) and cooled to 0° C. Triethyl phosphonoacetate (5.36 mL, 27.0 mmol) was added. Once the effervescence had subsided the mixture was stirred at 0° C. for 15 minutes. Cis 3,5-dimethylcyclohexanone (3.24 g, 25.7 mmol) was then added and the mixture allowed to warm to room temperature. After 1.5 hours the solvent was decanted from the thick oil which had formed and the oil washed with diethyl ether (3×50 mL). The decanted solvent and the ether washings were combined and washed with 2N HCl (50 mL) followed by brine (50 mL), dried (MgSO$_4$), and the solvent removed in vacuo to give a clear oil which was used without purification.

Trans-Nitro Ester

The α,β-unsaturated ester (2.08 g, 10.36 mmol) was dissolved in tetrahydrofuiran (20 mL) with nitromethane (1.12 mL, 20.7 mmol) and tetrabutylammonium fluoride (1.0 M in THF, 15.5 mL, 15.5 mmol) and the resulting mixture heated to 70° C. After 18 hours the mixture was diluted with ethyl acetate (50 mL) and washed with 2N HCl (40 mL) followed by brine (40 mL). The organic phase was separated, dried (MgSO$_4$), and the solvent removed in vacuo. The residue was purified by flash chromatography (silica, ethyl acetate:heptane, 1:9) to give 1.53 g (56%) as a colorless oil.

$^1$H NMR 400 MHz (CDCl$_3$) δ: 0.80–0.98 (10H, m), 1.27 (3H, t, J=6 Hz), 1.58–1.80(4H, m), 2.59(2H, s), 4.15 (2H, q, J=6 Hz), 4.57 (2H, s).

MS (APCI) m/e: 258 ([MH]$^+$; 12%)

IR thin film v (cm$^{-1}$): 1028, 1182, 1377, 1461, 1549, 1732, 2954.

Lactam

The nitro ester (1.495 g, 5.8 mmol) was dissolved in methanol (60 mL) and shaken over Raney nickel (catalytic) under an atmosphere of hydrogen gas (40 psi) at 35° C. After 18 hours the catalyst was removed by filtration through celite. The methanol was removed in vacuo to give 997 mg (95%) of a white solid. $^1$H NMR 400 MHz (CDCl$_3$) δ: 0.52 (1H, m), 0.80–0.98 (7H, m), 1.51 (2H, m), 1.69 (4H, m), 2.20 (2H, s), 3.09 (2H, s), 6.03 (1H, br s).

MS (APCI) m/e: 182 ([MH]$^+$; 100%)

IR thin film v (cm$^{-1}$): 1258, 1278, 1324, 1373, 1432, 1456, 1679, 1693, 2908, 3208.

C$_{11}$H$_{19}$NO calculated: C, 72.88%; H, 10.56%; N, 7.73%
Found: C, 72.76%; H, 10.74%; N, 7.61%

Amino Acid Hydrochloride

The lactam (981 mg, 5.4 mmol) was heated to reflux in a mixture of 6N HCl (15 ml,) and 1,4-dioxan (5 mL). After 4 hours the solvent was removed in vacuo and the solid residue recrystallized from a methanol/ethyl acetate/heptane mixture to give 516 mg (40%) of a white solid.

$^1$H NMR 400 MHz (d-6 DMSO) δ: 0.47 (1H, m), 0.77–0.91 (8H, m), 1.46–1.63 (5H, m), 2.45 (2H, s), 2.84 (2H, s), 8.00 (3H, br s), 12.37 (1H, br s).

MS (APCI) m/e: 200 ([MH–HCl]$^+$; 100%)

C$_{11}$H$_{22}$NO$_2$Cl calculated: C, 56.04%; H, 9.41%; N, 5.94%; Cl, 15.04%
Found: C, 56.00%; H, 9.40%; N, 6.09%; Cl, 15.09%

EXAMPLE 4

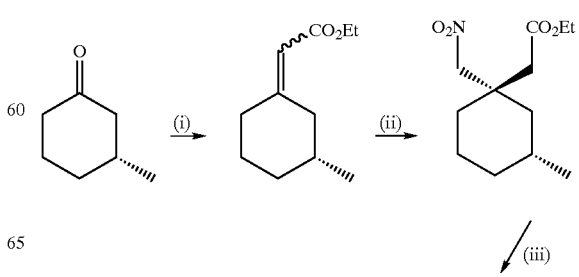

9

-continued

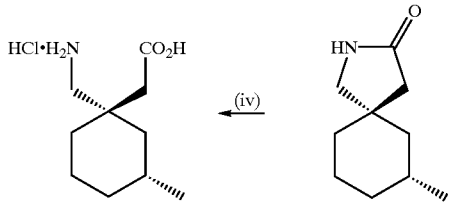 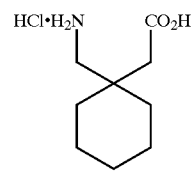

(i) (EtO)$_2$ P(O)CH$_2$CO$_2$Et, NaH, THF
(ii) MeNO$_2$, Bu$_4$N$^+$F$^-$, THF, 70° C.
(iii) Raney Ni, H$_2$, MeOH
(iv) HCl/H$_2$O α,β-unsaturated Ester Sodium hydride (60% dispersion in oil, 1.048 g, 26.2 mmol) was suspended in dry tetrahydrofuran (50 mL) and cooled to 0° C. Triethyl phosphonoacetate (4.76 mL, 23.9 mmol) was added. Once the effervescence had subsided the mixture was stirred at 0° C. for 15 minutes. 3R 3-methylcyclohexanone (2.45 g, 21.8 mmol) was then added and the mixture allowed to warm to room temperature. After 1.5 hours the solvent was decanted from the thick oil which had formed and diluted with diethyl ether (50 mL). The decanted solvent was washed with water (50 mL) followed by brine (50 mL), dried (MgSO$_4$), and the solvent removed in vacuo to give a clear oil which was used without purification.

Trans-Nitro Ester

The α,β-unsaturated ester (2.48 g, 13.6 mmol) was dissolved in tetrahydrofuran (20 mL) with nitromethane (1.96 mL, 27.2 mmol) and tetrabutylammonium fluoride (1.0 M in THF, 20.4 mL, 20.4 mmol) and the resulting mixture heated to 70° C. After 18 hours the mixture was diluted with ethyl acetate (50 mL) and washed with 1N HCl (2×25 mL) followed by brine (25 mL). The organic phase was separated, dried (MgSO$_4$), and the solvent removed in vacuo. The residue was purified by flash chromatography (silica, ethyl acetate:heptane, 1:10) to give 2.43 g (73%) as a colorless oil.

$^1$H NMR 400 MHz (CDCl$_3$) δ: 0.78–0.98 (4H, m), 1.27 (3H, t, J=6 Hz), 1.40–1.81 (8H, m), 2.61 (2H, s), 4.17 (2H, q, J=6 Hz), 4.58 (2H, s).

MS (APCI) m/e: 244 ([MH]$^+$; 10%)

IR thin film v (cm$^{-1}$): 1027, 1097, 1155, 1190, 1378, 1457, 1549, 1732, 2929.

Lactam

The nitro ester (2.01 g, 8.28 mmol) was dissolved in methanol (30 mL) and shaken over Raney nickel (catalytic) under an atmosphere of hydrogen gas (40 psi) at 35° C. After 3 hours the catalyst was removed by filtration through celite. The methanol was removed in vacuo and the residue purified by flash chromatography (silica, ethyl acetate) to give 902 mg (65%) of a white solid.

$^1$H NMR 400 MHz (CDCl$_3$) δ: 0.77–0.96 (4H, m), 1.18–1.52 (3H, m), 1.62–1.78 (5H, m), 2.22 (2H, s), 3.08 (2H, s), 5.82 (1H, br s).

MS (APC1) m/e: 168 ([MH]$^+$; 100%)

IR thin film v (cm$^{-1}$): 1252, 1455, 1698, 2920, 3220.

Amino Acid Hydrochloride

The lactam (0.858 mg, 5.1 mmol) was heated to reflux in a mixture of 6N HCl (10 mL). After 3 hours the mixture was stirred at room temperature for 18 hours. The solvent was removed in vacuo and the solid residue recrystallized from a methanol/ethyl acetate/heptane mixture to give 341 mg (30%) of a white solid.

10

$^1$H NMR 400 MHz (d-6 DMSO) δ: 0.74–0.91 (5H, m), 1.02–1.18 (1H, m), 1.38–1.65 (6H, m), 2.46 (2H, s), 2.84 (2H, s), 7.97 (3H, br s), 12.37 (1H, br s).

IR KBr disk v (cm$^{-1}$): 1187, 1214, 1400, 1515, 1710, 2922, 3370

C$_{11}$H$_{22}$NO$_2$Cl calculated: C, 54.30%; H, 9.04%; N, 6.33%; Cl, 16.06%

Found: C, 54.19%; 11, 8.99%; N, 6.27%; Cl, 16.01%

We claim:

1. A process for the preparation of a compound of formula

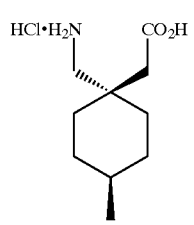

I which comprises:
   a) adding cyclohexanone to a mixture of sodium hydride suspended in dry tetrahydrofuran to which triethyl phosphonoacetate was added;
   b) partitioning the mixture between HCl and diethyl ether and collecting the ether layer;
   c) dissolving the product of step b) above, the α,β-unsaturated ester in THF with nitromethane and tetrabutylammonium fluoride and heating the resulting mixture to produce a nitro ester;
   d) dissolving the product of step c) above, a nitro ester in methanol and shaking over a catalyst to produce the corresponding lactam; and
   e) heating the product of step d) above, a lactam, to reflux in a mixture of HCl and dioxan to produce a compound of formula I, and converting, if desired, to a pharmaceutically acceptable salt.

2. A process for the preparation of a compound of formula

II which comprises:
   a) adding 4-methylcyclohexanone to a mixture of sodium hydride suspended in dry tetrahydrofuran to which triethyl phosphonoacetate was added to produce a mixture;
   b) decanting the solvent from the mixture step a) above to produce an α,β-unsaturated ester;
   c) dissolving the ester from step b) above in nitromethane and heating the resulting mixture;
   d) dissolving the nitro ester from step c) above in methanol and shaking over a catalyst to produce the corresponding lactam; and
   e) heating the product of step d) above to reflux in a mixture of HCl and dioxan to produce a compound of formula II above and converting, if desired, to a pharmaceutically acceptable salt.

3. A process for the preparation of a compound of formula III

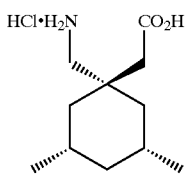

which comprises:
 a) adding cis 3,5-dimethylcyclohexanone to a mixture of sodium hydride suspended in dry tetrahydrofuran to which triethyl phosphonoacetate was added to produce a mixture;
 b) decanting the solvent from the mixture of step a) above to produce an α,β-unsaturated ester;
 c) dissolving the product of step b) above in nitromethane and heating the resulting mixture;
 d) dissolving the nitro ester from step c) above in methanol and shaking over a catalyst to produce the corresponding lactam; and
 e) heating the product of step d) above, a lactam, to reflux in HCl and dioxan to produce a compound of formula III above and converting, if desired, to a pharmaceutically acceptable salt thereof.

4. A process for the preparation of a compound of formula IV

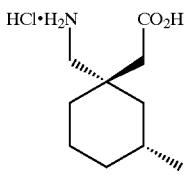

which comprises:
 a) adding 3R 3-methylcyclohexanone to a mixture of sodium hydride suspended in dry tetrahydrofuran to which triethyl phosphonoacetate was added to produce a mixture;
 b) decanting the solvent from the mixture of step a) above to produce the corresponding α,β-unsaturated ester;
 c) dissolving the ester from step b) above in nitromethane and heating the resulting mixture;
 d) dissolving the nitro ester from step c) above in methanol and shaking over a catalyst to produce the corresponding lactam; and
 e) heating the product of step d) above to reflux in a mixture of HCl and 1,4-dioxane to produce a compound of formula IV above and converting, if desired, to a pharmaceutically acceptable salt thereof.

5. A process for the preparation of a compound of formula IV

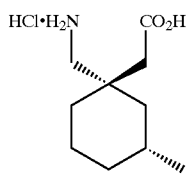

which comprises:
 a) adding 3R 3-methylcyclohexanone to a mixture of a base selected from sodium hydride, potassium hydride, lithium- or sodium- or potassium-hexamethyldisilazide, butyllithium or potassium t-butoxide suspended in a solvent selected from tetrahydrofuran, dimethylformamide, diethylether, or dimethylsulfoxide to which trialkylphosphonoacetate was added to produce a mixture at a temperature of from −78° C. to 100° C.;
 b) decanting the solvent from the mixture of step a) above to produce the corresponding α,β-unsaturated ester;
 c) dissolving the ester from step b) above in a solvent selected from tetrahydrofuran, diethylether, dimethylformamide, dimethylsulfoxide, benzene, toluene, dichloromethane, chloroform, or tetrachloromethane with nitromethane and a base selected from tetrabutylammonium fluoride, tetramethylguanidine, 1,5-diazabicyclo-[4,3,0]non-5-ene, 1,8-diazabicyclo[5,4,0]undec-7-ene, a sodium or potassium alkoxide, sodium hydride or potassium fluoride and heating the resulting mixture to a temperature of from −20° C. to 100° C.;
 d) dissolving the nitro ester from step c) above in a solvent selected from methanol, ethanol, isopropanol, ethyl acetate, acetic acid, 1,4-dioxane, chloroform or diethyl ether at a temperature of from 20° C. to 80° C. and shaking over a catalyst selected from Raney nickel, palladium on charcoal, or rhodium catalyst or a nickel or palladium containing catalyst under an atmosphere of hydrogen gas to product the corresponding lactam; and
 e) heating the product of step d) above to a temperature of from 20° C. to reflux in a mixture of HCl and a cosolvent selected from tetrahydrofuran, 1,4dioxane, of an inert water miscible solvent to produce a compound of Formula IV above and converting, if desired, to a pharmaceutically acceptable salt thereof.

* * * * *

UNITED STATES PATENT AND TRADEMARK OFFICE
CERTIFICATE OF CORRECTION

PATENT NO.   : 6,465,689 B1
DATED        : October 15, 2002
INVENTOR(S)  : Bryans et al.

It is certified that error appears in the above-identified patent and that said Letters Patent is hereby corrected as shown below:

<u>Column 12,</u>
Line 48, "1,4dioxane, of" should read -- 1,4-dioxane, or --.

Signed and Sealed this

Eleventh Day of March, 2003

JAMES E. ROGAN
*Director of the United States Patent and Trademark Office*